(12) United States Patent
Ghajar et al.

(10) Patent No.: US 12,059,207 B2
(45) Date of Patent: *Aug. 13, 2024

(54) COGNITIVE TRAINING SYSTEM WITH BINOCULAR COORDINATION ANALYSIS AND COGNITIVE TIMING TRAINING FEEDBACK

(71) Applicant: NeuroSync, Inc., Holliston, MA (US)

(72) Inventors: Jamshid Ghajar, Palo Alto, CA (US); Jianliang Tong, Newark, NJ (US); Jun Maruta, New York, NY (US)

(73) Assignee: NEUROSYNC, INC., Holliston, MA (US)

( * ) Notice: Subject to any disclaimer, the term of this patent is extended or adjusted under 35 U.S.C. 154(b) by 123 days.

This patent is subject to a terminal disclaimer.

(21) Appl. No.: 17/515,292

(22) Filed: Oct. 29, 2021

(65) Prior Publication Data
US 2022/0047158 A1    Feb. 17, 2022

Related U.S. Application Data

(63) Continuation of application No. 14/454,662, filed on Aug. 7, 2014, now abandoned.
(Continued)

(51) Int. Cl.
*A61B 3/113* (2006.01)
*A61B 3/032* (2006.01)
(Continued)

(52) U.S. Cl.
CPC ............. *A61B 3/113* (2013.01); *A61B 3/032* (2013.01); *A61B 3/085* (2013.01); *A61B 3/111* (2013.01);
(Continued)

(58) Field of Classification Search
CPC ......... A61B 3/113; A61B 3/032; A61B 3/085; A61B 3/111; A61B 5/165; A61B 5/168; A61B 5/163
See application file for complete search history.

(56) References Cited

U.S. PATENT DOCUMENTS

| 4,332,566 A | 6/1982 | Mazeski et al. |
| 4,407,299 A | 10/1983 | Culver |

(Continued)

FOREIGN PATENT DOCUMENTS

| EP | 1726260 A2 | 11/2006 |
| EP | 2095759 A1 | 9/2009 |
| GB | 2496005 A | 5/2013 |

OTHER PUBLICATIONS

Ball, "The Role of Higher-Order Motor Areas in Voluntary Movement as Revealed by High-Resolution EEG and fMRI," NeuroImage 10, 662-694 (1999), Article ID nimg. 1999-0507, available online at http://www.idealibrary.com, 13 pgs.
(Continued)

*Primary Examiner* — David J. McCrosky
(74) *Attorney, Agent, or Firm* — Morgan, Lewis & Bockius LLP

(57) ABSTRACT

A method of testing a subject for impairment includes presenting the subject with a display of a smoothly moving object, repeatedly moving over a tracking path and, while presenting the display to the subject, measuring the subject's right eye positions and measuring the subject's left eye positions. The method further includes generating a disconjugacy metric by comparing the measured right eye positions with the measured left eye positions, comparing the disconjugacy metric with a predetermined baseline to determine whether the disconjugacy metric is indicative of an impairment, and generating a report based on the disconjugacy metric.

12 Claims, 9 Drawing Sheets

Related U.S. Application Data

(60) Provisional application No. 61/865,546, filed on Aug. 13, 2013.

(51) Int. Cl.
*A61B 3/08* (2006.01)
*A61B 3/11* (2006.01)
*A61B 5/16* (2006.01)

(52) U.S. Cl.
CPC .............. *A61B 5/163* (2017.08); *A61B 5/165* (2013.01); *A61B 5/168* (2013.01)

(56) References Cited

U.S. PATENT DOCUMENTS

| | | | |
|---|---|---|---|
| 4,838,681 A | 6/1989 | Pavlidis | |
| 4,885,687 A | 12/1989 | Carey | |
| 4,889,422 A | 12/1989 | Pavlidis | |
| 5,070,883 A | 12/1991 | Kasahara | |
| 5,137,027 A | 8/1992 | Kasahara | |
| 5,331,969 A | 7/1994 | Silberstein | |
| 5,491,492 A | 2/1996 | Knapp et al. | |
| 5,529,498 A | 6/1996 | Cassily et al. | |
| 5,649,061 A | 7/1997 | Smyth | |
| 5,662,117 A | 9/1997 | Bittman | |
| 5,743,744 A | 4/1998 | Cassily et al. | |
| 5,867,587 A | 2/1999 | Aboutalib et al. | |
| 5,942,954 A | 8/1999 | Galiana et al. | |
| 6,090,051 A | 7/2000 | Marshall | |
| 6,102,870 A | 8/2000 | Edwards | |
| 6,162,186 A | 12/2000 | Scinto et al. | |
| 6,231,187 B1 | 5/2001 | Munoz et al. | |
| 6,542,081 B2 | 4/2003 | Torch | |
| 6,575,902 B1 | 6/2003 | Burton | |
| 6,603,491 B2 | 8/2003 | Lemelson et al. | |
| 7,384,399 B2 | 6/2008 | Ghajar | |
| 7,390,091 B2 | 6/2008 | Clemons et al. | |
| 7,500,752 B2 | 3/2009 | Nashner | |
| 7,819,818 B2 | 10/2010 | Ghajar | |
| 8,866,809 B2 | 10/2014 | McCarthy | |
| 9,072,481 B2 | 7/2015 | Shelhamer | |
| 9,078,598 B2 | 7/2015 | French et al. | |
| 9,958,939 B2 | 5/2018 | Ghajar | |
| 10,365,714 B2 | 7/2019 | Ghajar | |
| 11,199,899 B2 | 12/2021 | Ghajar | |
| 11,317,861 B2 * | 5/2022 | Ghajar ................... | A61B 5/168 |
| 2002/0099305 A1 | 7/2002 | Fukushima et al. | |
| 2003/0225342 A1 | 12/2003 | Hong et al. | |
| 2005/0177065 A1 | 8/2005 | Ghajar | |
| 2006/0139319 A1 | 6/2006 | Kariathungal et al. | |
| 2006/0270945 A1 | 11/2006 | Ghajar | |
| 2007/0017534 A1 | 1/2007 | Thorpe | |
| 2007/0236663 A1 | 10/2007 | Waldorf et al. | |
| 2009/0115965 A1 | 5/2009 | Waldorf et al. | |
| 2010/0039617 A1 | 2/2010 | Martinez-Conde et al. | |
| 2010/0094161 A1 | 4/2010 | Kiderman et al. | |
| 2010/0167246 A1 | 7/2010 | Ghajar | |
| 2010/0280372 A1 | 11/2010 | Poolman et al. | |
| 2010/0292545 A1 | 11/2010 | Berka et al. | |
| 2012/0314045 A1 | 12/2012 | Billard et al. | |
| 2013/0002846 A1 | 1/2013 | De Bruijn et al. | |
| 2013/0091515 A1 | 4/2013 | Sakata et al. | |
| 2013/0194177 A1 | 8/2013 | Sakata | |
| 2013/0230252 A1 | 9/2013 | Hung et al. | |
| 2013/0230253 A1 | 9/2013 | Stankiewicz et al. | |
| 2013/0233097 A1 | 9/2013 | Hayner et al. | |
| 2013/0300654 A1 | 11/2013 | Seki | |
| 2013/0321265 A1 | 12/2013 | Bychkov et al. | |
| 2014/0154651 A1 | 6/2014 | Stack | |
| 2014/0255888 A1 | 9/2014 | Stack | |
| 2014/0313488 A1 | 10/2014 | Kiderman et al. | |
| 2014/0327880 A1 | 11/2014 | Kiderman et al. | |
| 2014/0330159 A1 | 11/2014 | Costa et al. | |
| 2014/0347265 A1 | 11/2014 | Aimone et al. | |
| 2015/0130703 A1 | 1/2015 | Ghajar | |
| 2015/0051508 A1 | 2/2015 | Ghajar et al. | |
| 2015/0062534 A1 | 3/2015 | Massengill | |
| 2015/0077543 A1 | 3/2015 | Kerr et al. | |
| 2015/0097826 A1 | 4/2015 | McCarthy | |
| 2015/0141865 A1 | 5/2015 | Nakajima et al. | |
| 2015/0213725 A1 | 7/2015 | Huntley et al. | |
| 2015/0277710 A1 | 10/2015 | Lee et al. | |
| 2015/0338915 A1 | 11/2015 | Publicover et al. | |
| 2016/0022137 A1 | 1/2016 | Wetzel et al. | |
| 2016/0070439 A1 | 3/2016 | Bostick et al. | |
| 2016/0077547 A1 | 3/2016 | Aimone et al. | |
| 2016/0106315 A1 | 4/2016 | Kempinski | |
| 2016/0132726 A1 | 5/2016 | Kempinski et al. | |
| 2016/0262608 A1 | 9/2016 | Krueger | |
| 2016/0299505 A1 | 10/2016 | Ohara | |
| 2016/0371726 A1 | 12/2016 | Yamaji et al. | |
| 2016/0379261 A1 | 12/2016 | Avalos et al. | |
| 2017/0123492 A1 | 5/2017 | Marggraff et al. | |
| 2017/0258397 A1 * | 9/2017 | Ghajar ................... | A61B 3/111 |
| 2017/0337476 A1 | 11/2017 | Gordon et al. | |
| 2018/0115673 A1 | 4/2018 | Yamasaki et al. | |
| 2018/0133504 A1 | 5/2018 | Malchano et al. | |
| 2018/0196511 A1 | 7/2018 | Chae | |
| 2018/0210546 A1 | 7/2018 | Rawlinson et al. | |
| 2018/0314328 A1 | 11/2018 | Ghajar | |
| 2019/0079917 A1 | 3/2019 | Berzak et al. | |
| 2019/0236386 A1 | 8/2019 | Yu et al. | |
| 2019/0250408 A1 | 8/2019 | Lafon et al. | |
| 2019/0265802 A1 | 8/2019 | Parshionikar | |
| 2020/0089317 A1 | 3/2020 | Ghajar | |
| 2020/0226941 A1 | 7/2020 | Kakaraparthy et al. | |

OTHER PUBLICATIONS

Barnes, "Anticipatory Control of Hand and Eye Movements in Humans During Oculo-Manual Tracking," Journal of Physiology (2002), 539.1, The Physiological Society 2002, 14 pgs.

Chan, "Are There Sub-Types of Attentional Deficits in Patients with Persisting Post-Concussive Symptoms? A Cluster Analytical Study," Brain Injury, 2003, vol. 17, No. 2, 18 pgs.

Cronin-Golomb, et al., "Visual dysfunction in Alzheimer's disease: relation to normal aging," Annals of neurology 29.1 (1991): 41-52.

"Eye Tracking," downloaded from http://en.wikipedia.org/wiki/eye_tracking, on Jun. 27, 2008, 5 pgs.

Sync-Think, Inc., Office Action, EP06813639.9, May 31, 2011, 4 pgs.

Gibbon, "Toward a Neurobiology of Temporal Cognition: Advances and Challenges, Current Opinion in Neurobiology," (1997) 7:170-184, 16 pgs.

Glenstrup et al., "2 Present-day Eye-Gaze Tracking Techniques," downloaded from http://www.diku.dk/~panic/eyegaze/node8.html on Jun. 27, 2008, 3 pgs.

Gredeback, "The Development of Two-Dimensional Tracking: A Longitudinal Study of Circular Pursuit," Exp. Brain Res. (2005) 163:204-213, 10 pgs.

Green, "Deficits in Facial Emotion Perception in Adults with Recent Traumatic Brain Injury," Neuropsychologia, (2004) 42:133-141, 9 pgs.

Hulsmann, "From Will to Action: Sequential Cerebellar Contributions to Voluntary Movement," NeuroImage, (2003) 20:1485-1492, 18 pgs.

Sync-Think, Inc., International Search Report and Written Opinion, PCT/US2006/032773, Jan. 22, 2007, 11 pgs.

"Jonny Chung Lee>Projects>Wii," downloaded from http://www.cs.cmu.edu/~johnny/projects/wii/ on Jun. 28, 2008, 2 pgs.

Jonny Chung Lee, "Procrastineering giving into productive distractions," downloaded from http://procrastineering.blogspot.com/2007/12/wiimote.desktopvr~faq . . . , 4 pgs.

Kathmann, "Deficits in Gain of Smooth Pursuit Eye Movements in Schizophrenia and Affective Disorder Patients and Their Unaffected Relatives," Am J. Psychiatry 160:4, Apr. 2003, 8 pgs.

Kim et al., "Vision-Based Eye-Gaze Tracking for Human Computer Interface," 0-7803-5731-0/99, 1999 IEEE, pp. 324-329.

(56) References Cited

OTHER PUBLICATIONS

Kumar, Manu, "Gaze-enhanced User Interface Design," downloaded from http://hci.stanford.edu.reasearch/GUIDe/on Jun. 27, 2008, 2 pgs.
Lane, D.M., "Measures of Variability," Online Stat Book, Internet Archive, Dec. 27, 2012, retrieved from <http://web-beta.archive.org/web/20121227105126/http://onlinestatbook.com/2/summarizing_distributions/variability.html> on Mar. 28, 2017, 4 pgs.
Lewine, "Neuromagnetic Assessment of Pathophysiologic Brain Activity Induced by Minor Head Trauma," AJNR Am. J. Neuroradiol., (May 1999) 20:857-866, 10 pgs.
Lutz, "Guiding the Study of Brain Dynamics by Using First-Person Data: Synchrony Patterns Correlate with Ongoing Conscious States During a Simple Visual Task," PNAS, (Feb. 5, 2002) 99(3):1586-1591, 6 pgs.
Madelain, "Effects of Learning on Smooth Pursuit During Transient Disappearance of a Visual Target," J. Neurophysiol., (2003) 90:972-982, 11 pgs.
Mangels, "Effects of Divided Attention on Episodic Memory in Chronic Traumatic Brain Injury: A Function of Severity and Strategy," Neuropsychologia, (2002) 40:2369-2385, 17 pgs.
Mehta, "Forward Models in Visuomotor Control," J. Neurophysiol., (2002) 88:942-953, 12 pgs.
Pedersen, "Origin of Human Motor Readiness Field Linked to Left Middle Frontal Gyrus by MEG and PET," NeuroImage 8, 214-220 (1998), Article No. NI980362, 7 pgs.
Perbal, "Relationships Between Time Estimation, Memory, Attention, and Processing Speed in Patients with Severe Traumatic Brain Injury," Neuropsychologia, (2003) 41:1599-1610, 13 pgs.
Semmlow, John L., Gabriel M. GauthieR, and Jean-Louis Vercher. "Short term adaptive modification of saccadic amplitude." Eye Movements from Physiology to Cognition. Elsevier, 1987. 191-200. (Year: 1987).
Smith, "A Right Hemispheric Frontocerebellar Network for Time Discrimination of Several Hundreds of Milliseconds," NeuroImage, (2003) 20:344-350, 7 pgs.
Squeri, Valentina et al., "Force-field compensation in a manual tracking task," PLoS One Jun. 2010, vol. 5, No. 6, e11189, 12 pgs.
Strauss, "Intraindividual Variability in Cognitive Performance in Three Groups of Older Adults: Cross-Domain Links to Physical Status and Self-Perceived Affect and Beliefs," Journal of the International Neuropsychological Society (2002), 8, 893-906, 14 pgs.
Sync-Think, Inc., International Search Report and Written Opinion, PCT/US2014/050774, Nov. 12, 2014, 13 pgs.
Sync-Think, Inc., International Preliminary Report on Patentability, PCT/US2014/050774, Feb. 16, 2016, 9 pgs.
Sync-Think, Inc., International Search Report, PCT/US2016/027923, Jul. 7, 2016, 13 pgs.
Sync-Think, Inc., International Preliminary Report on Patentability, PCT/US2016/027923, Oct. 17, 2017, 9 pgs.
Sync-Think, Inc., Communication Pursuant to Rules 161(1) and 162, EP14755513.0, Mar. 23, 2016, 2 pgs.
Sync-Think, Inc., Communication Pursuant to Article 94(3), EP14755513.0, Mar. 1, 2017, 5 pgs.
Sync-Think, Inc., Communication Pursuant to Article 94(3), EP14755513.0, Dec. 21, 2017, 8 pgs.
"The Exploratorium: seeing/seeing in context," downloaded from http://www.exploratorium.edu/seeing/about/seeing_attention.html on Jun. 28, 2008, 2 pgs.
Ross et al., "Anticipatory saccades during smooth pursuit eye movements and familial transmission of schizophrenia." Biological Psychiatry 44.8 (1998): 690-697.
Jamshid Ghajar, Non-Final Office Action, U.S. Appl. No. 16/525,425, Feb. 10, 2021, 23 pgs.
Jamshid Ghajar, Notice of Allowance, U.S. Appl. No. 16/525,425, Aug. 11, 2021, 17 pgs.
Ghajar, Non-Final Office Action, U.S. Appl. No. 15/585,057, Jul. 19, 2019, 10 pgs.
Weber, K.P., et al., "Head Impulse Test in Unilateral Vestibular Loss: Vestibular-Ocular Reflex and Catch-Up Saccades." Neurology 70.6 (2008): 454-463. (Year: 2008).
Ghajar, Final Office Action, U.S. Appl. No. 15/585,057, Mar. 9, 2020, 10 pgs.
Maruta, Non-Final Office Action, U.S. Appl. No. 15/099,427, Mar. 12, 2018, 16 pgs.
McCrosky, Non-Final Office Action, U.S. Appl. No. 16/099,427, Jun. 21, 2019, 7 pgs.
Maruta, Final Office Action, U.S. Appl. No. 15/099,427, Jan. 17, 2020, 11 pgs.
Ghajar, Non-Final Office Action, U.S. Appl. No. 14/454,662, Mar. 28, 2016, 15 pgs.
Ghajar, Non-Final Office Action, U.S. Appl. No. 14/454,662, Sep. 16, 2016, 15 pgs.
Ghajar, Non-Final Office Action, U.S. Appl. No. 14/454,662, Apr. 4, 2017, 18 pgs.
Ghajar, Final Office Action, U.S. Appl. No. 14/454,662, Sep. 13, 2017, 21 pgs.
Ghajar, Non-Final Office Action, U.S. Appl. No. 14/454,662, Jan. 8, 2020, 9 pgs.
Ghajar, Non-Final Office Action, U.S. Appl. No. 14/552,190, Sep. 19, 2016, 10 pgs.
Ghajar, Final Office Action, U.S. Appl. No. 14/552,190, Apr. 3, 2017, 15 pgs.
Ghajar, Non-Final Office Action, U.S. Appl. No. 14/552,190, Dec. 14, 2017, 16 pgs.
Ghajar, Final Office Action, U.S. Appl. No. 14/552,190, Jul. 16, 2018, 17 pgs.
Ghajar, Non-Final Office Action, U.S. Appl. No. 14/552,190, Jan. 8, 2020, 12 pgs.
Zuber, B.L., J.L. Semmlow, and L. Stark. "Frequency Characteristics of the Saccadic Eye Movement." Biophysical Journal 8.11 (1968): 1288-1298. (Year: 1968).
Tatler, Benjamin W., Roland J. Baddeley, and Benjamin T. Vincent. "The Long and the Short of it: Spatial Statistics at Fixation Vary with Saccade Amplitude and Task." Vision Research 46.12 (2006): 1857-1862. (Year: 2006).

\* cited by examiner

COGNITIVE TRAINING SYSTEM WITH BINOCULAR COORDINATION ANALYSIS AND COGNITIVE TIMING TRAINING FEEDBACK

RELATED APPLICATIONS

This application is a continuation of U.S. patent application Ser. No. 14/454,662, filed Aug. 7, 2014, which claimed priority to U.S. Provisional Application No. 61/865,546, filed Aug. 13, 2013, entitled "System and Method for Cognition and Oculomotor Impairment Diagnosis Using Binocular Coordination Analysis," each of which is incorporated herein by reference in its entirety.

This application is related to U.S. application Ser. No. 11/245,305, filed Oct. 5, 2005, entitled "Cognition and Motor Timing Diagnosis Using Smooth Eye Pursuit Analysis," which is incorporated herein by reference in its entirety.

TECHNICAL FIELD

The disclosed embodiments relate generally to systems and methods of testing a person's ability to track and anticipate stimuli. More specifically, to a method and system for cognition and oculomotor impairment diagnosis using binocular coordination analysis.

BACKGROUND

Pairing an action with anticipation of a sensory event is a form of attention that is crucial for an organism's interaction with the external world. The accurate pairing of sensation and action is dependent on timing and is called sensory-motor timing, one aspect of which is anticipatory timing. Anticipatory timing is essential to successful everyday living, not only for actions but also for thinking. Thinking or cognition can be viewed as an abstract motor function and therefore also needs accurate sensory-cognitive timing. Sensory-motor timing is the timing related to the sensory and motor coordination of an organism when interacting with the external world. Anticipatory timing is usually a component of sensory-motor timing and is literally the ability to predict sensory information before the initiating stimulus.

Anticipatory timing is essential for reducing reaction times and improving both movement and thought performance. Anticipatory timing only applies to predictable sensory-motor or sensory-thought timed coupling. The sensory modality (i.e., visual, auditory etc.), the location, and the time interval between stimuli, must all be predictable (i.e., constant, or consistent with a predictable pattern) to enable anticipatory movement or thought.

Without reasonably accurate anticipatory timing, a person cannot catch a ball, know when to step out of the way of a moving object (e.g., negotiate a swinging door), get on an escalator, comprehend speech, concentrate on mental tasks or handle any of a large number of everyday tasks and challenges. This capacity for anticipatory timing can become impaired with sleep deprivation, aging, alcohol, drugs, hypoxia, infection, clinical neurological conditions including but not limited to Attention Deficit Hyperactivity Disorder (ADHD), schizophrenia, autism and brain trauma (e.g., a concussion). For example, brain trauma may significantly impact a person's cognition timing, one aspect of which is anticipatory timing. Sometimes, a person may appear to physically recover quickly from brain trauma, but have significant problems with concentration and/or memory, as well as having headaches, being irritable, and/or having other symptoms as a result of impaired anticipatory timing. In addition, impaired anticipatory timing may cause the person to suffer further injuries by not having the timing capabilities to avoid accidents.

SUMMARY

Accordingly, there is a need to test a subject's sensory-motor timing and especially a subject's anticipatory timing. Therefore, in accordance with some embodiments, a method, system, and computer-readable storage medium are proposed for cognition and oculomotor impairment diagnosis using binocular coordination analysis.

Some implementations provide a method for cognition and oculomotor impairment diagnosis using binocular coordination analysis. The method includes presenting the subject with a display of a smoothly moving object, repeatedly moving over a tracking path and, while presenting the display to the subject, measuring the subject's right eye positions and measuring the subject's left eye positions. The method further includes generating a disconjugacy metric by comparing the measured right eye positions with the measured left eye positions, comparing the disconjugacy metric with a predetermined baseline to determine whether the disconjugacy metric is indicative of an impairment, and generating a report based on the disconjugacy metric.

In some implementations, the disconjugacy metric corresponds to a standard deviation of differences between the subject's right eye position and the subject's left eye position over a duration of the presentation.

In some implementations, the predetermined baseline is based on at least one of: a disconjugacy range associated with a preselected group of control subjects, wherein the preselected group of control subjects have normal conjugate gaze; and a disconjugacy metric for the subject generated from a previous test.

In some implementations, the method further comprises presenting a distraction to the subject while presenting the subject with the display of the smoothly moving object; generating a metric of distractibility, where the metric of distractibility is indicative of the subject's susceptibility to distraction; and where the generated report is further based on the metric of distractibility. In some implementations, the distraction is an unpredictable sound. In some implementations the distraction is a visual stimulus.

In some implementations, the display of the smoothly moving object includes a plurality of pseudorandom gaps, where, during a respective pseudorandom gap in the plurality of pseudorandom gaps, the object is not displayed; the method further includes generating a stressed disconjugacy metric, where the stressed disconjugacy metric is indicative of whether the subject has a stress-sensitive impairment; and where the generated report is further based on the stressed disconjugacy metric.

In some implementations, a respective pseudorandom gap comprises a pseudorandom starting point on the tracking path and a pseudorandom duration.

In some implementations, the method includes comparing the stressed disconjugacy metric with the disconjugacy metric to determine whether the subject has a stress-sensitive impairment.

In some implementations, the method includes, while presenting the subject with a display of a smoothly moving object, measuring the subject's eye movements; comparing the measured eye movements with movements of the smoothly moving object to generate a tracking metric, where the tracking metric corresponds to how accurately and how consistently the subject visually tracks movement of the object; and where the generated report is further based on the tracking metric.

In some implementations, the tracking metric is generated based on at least one of: a variability of eye position error metric; a variability of eye velocity gain metric; an eye position error metric; a rate or number of saccades metric; and a visual feedback delay metric.

In some implementations, the impairment is a cognitive impairment. In some implementations, the impairment is an oculomotor impairment.

In some implementations, measuring the subject's eye positions is accomplished using one or more video cameras.

In some implementations, the method includes repeating the presenting, generating, and comparing operations multiple times so as to generate a sequence of subject feedback signals, thereby enabling the subject to adjust their response to the stimuli in accordance with the subject feedback signals.

In accordance with some implementations, a system includes one or more processors, memory, and one or more programs stored in the memory. The one or more programs comprising instructions to present the subject with a display of a smoothly moving object, repeatedly moving over a tracking path and, while presenting the display to the subject, measure the subject's right eye positions and measure the subject's left eye positions. The one or more programs further comprise instructions to generate a disconjugacy metric by comparing the measured right eye positions with the measured left eye positions; compare the disconjugacy metric with a predetermined baseline to determine whether the disconjugacy metric is indicative of an impairment; and generate a report based on the disconjugacy metric.

In some implementations, the system further comprises a display on which the smoothly moving object is displayed and a measurement apparatus to measure the subject's right eye positions and the subject's left eye positions.

In accordance with some implementations, an electronic device is provided that comprises one or more processors and memory storing one or more programs for execution by the one or more processors, the one or more programs including instructions for performing any of the methods described herein.

In accordance with some implementations, a computer-readable storage medium (e.g., a non-transitory computer readable storage medium) is provided, the computer-readable storage medium storing one or more programs for execution by one or more processors of an electronic device, the one or more programs including instructions for performing any of the methods described herein.

In accordance with some implementations, a method includes receiving measurements of a subject's right eye positions and measurements of the subject's left eye positions, where the measurements correspond to the subject watching a display of a smoothly moving object, repeatedly moving over a tracking path. The method further includes generating a disconjugacy metric by comparing the measured right eye positions with the measured left eye positions, comparing the disconjugacy metric with a predetermined baseline to determine whether the disconjugacy metric is indicative of an impairment, and generating a report based on the disconjugacy metric.

BRIEF DESCRIPTION OF THE DRAWINGS

Like reference numerals refer to corresponding parts throughout the several views of the drawings.

DETAILED DESCRIPTION OF EMBODIMENTS

It is very difficult to measure thinking performance without a movement. However, since a similar neural network is used for anticipatory timing, cognition and motor timing are linked. Therefore diagnosis and therapy can be performed for anticipatory timing difficulties in the motor and cognitive domains using motor reaction times and accuracy. In particular, both the reaction time and accuracy of a subject's movements can be measured. As discussed below, these measurements can be used for both diagnosis and therapy.

Anticipatory cognition and movement timing are controlled by essentially the same brain circuits. Variability or a deficit in anticipatory timing produces imprecise movements and disrupted thinking, such as difficulty in concentration, memory recall, and carrying out both basic and complex cognitive tasks. Such variability and/or deficits leads to longer periods of time to successfully complete tasks and also leads to more inaccuracy in the performance of such tasks. Accordingly, in some embodiments, such variability is measured to determine whether a person suffers impaired anticipatory timing. In some embodiments, a sequence of stimuli is used in combination with a feedback mechanism to train a person to improve anticipatory timing.

Sequenced stimuli presented to a subject may include sequences of both predictable and non-predictable (e.g., random or pseudo-random) stimuli. In one embodiment, the non-predictable stimuli are presented to a subject before the predictable stimuli. The stimuli can use any sensory modality. In some embodiments, the stimuli are visual stimuli. In other embodiments, the stimuli are auditory. While other forms of stimuli can be used, the embodiments described here use visual stimuli. The subject's responses may be visual, manual or even spoken. In some embodiments, the subject's responses are measured by a mechanical, piezoelectric or other sensors activated by physical movement of the subject, such as pressing a button. In yet other embodiments, a frontal brain electroencephalographic (EEG) signal (e.g., the "contingent negative variation" signal) is measured during the period before a subject's response. The amplitude of the EEG signal is proportional to the degree of anticipation and will be disrupted when there are anticipatory timing deficits. In the embodiments described below, the subject's responses are measured by tracking eye movement.

Figure 1:
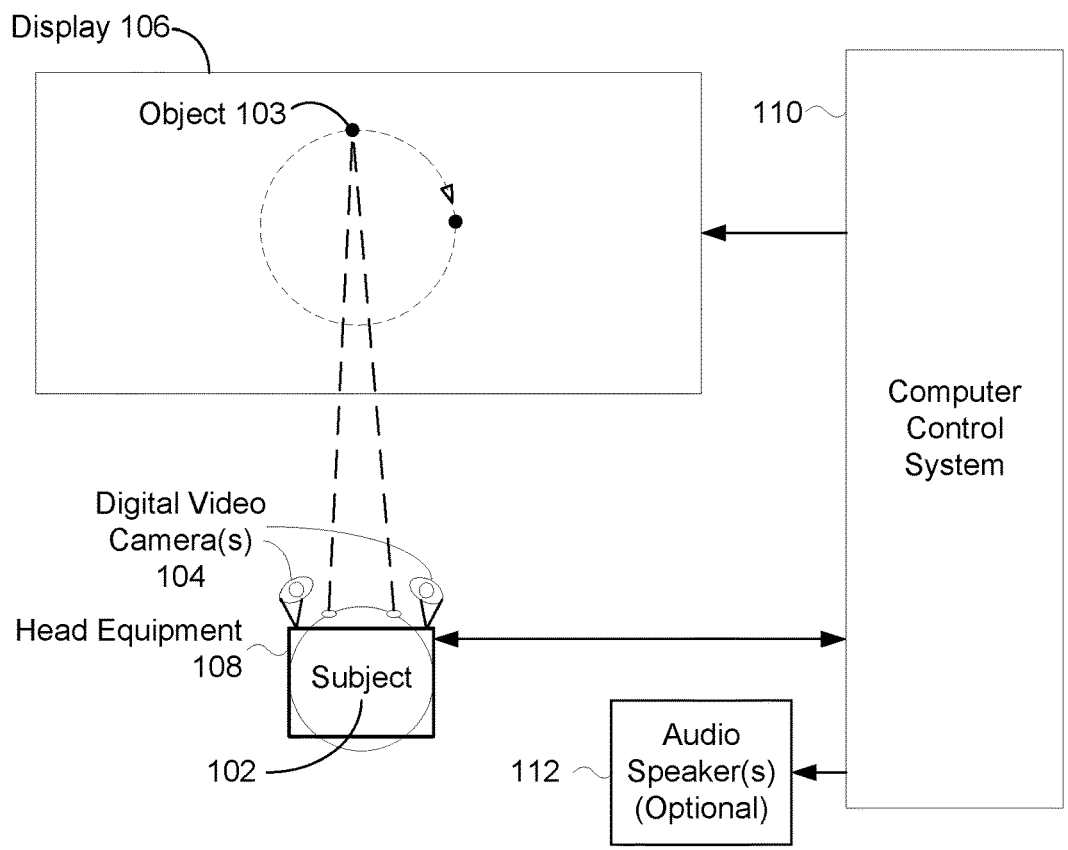
FIG. 1 is a block diagram illustrating a system for measuring a subject's ability to visually track a smoothly moving object in accordance with some embodiments.

FIG. 1 illustrates a system for measuring a subject's ability to visually track a smoothly moving object in accordance with some embodiments. Subject 102 is shown smoothly moving image 103 (e.g., a dot or ball moving at a constant speed), following a path (e.g., a circular or oval path) on display 106 (e.g., a screen). Digital video cameras 104 are focused on subject 102's eyes so that eye positions (and, in some embodiments, eye movements) of subject 102 are recorded. In accordance with some embodiments, digital video cameras 104 are mounted on subject 102's head by head equipment 108 (e.g., a headband). Various mechanisms are, optionally, used to stabilize subject 102's head, for instance to keep the distance between subject 102 and display 106 fixed, and to also keep the orientation of subject 102's head fixed as well. In one embodiment, the distance between subject 102 and display 106 is kept fixed at approximately 40 cm. In some implementations, head equipment 108 includes the head equipment and apparatuses described in U.S. Patent Publication 2010/0204628 A1, which is incorporated by reference in its entirety.

Display 106 is, optionally, a computer monitor, projector screen, or other display device. Display 106 and digital video cameras 104 are coupled to computer control system 110. In some embodiments, computer control system 110 controls the patterns displayed and also receives and analyses the eye position information received from the digital video cameras 104.

Figure 2:
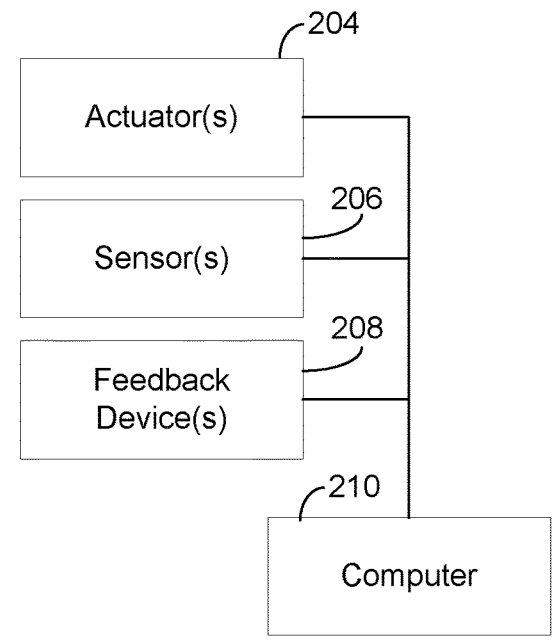
FIG. 2 is a conceptual block diagram illustrating a cognition timing diagnosis and training system in accordance with some embodiments.

FIG. 2 illustrates a conceptual block diagram of a cognition diagnosis and training system in accordance with some embodiments. Cognitive diagnosis and training system 200 includes computer 210 (e.g., computer control system 110) coupled to one or more actuators 204, and one or more sensors 206. In some embodiments, system 200 includes one or more feedback devices 208 (e.g., when system 200 is configured for use as a cognitive timing training system). In some embodiments, feedback is provided to the subject via the actuators 204. In some embodiments, actuators 204 include a display device for presenting visual stimuli to a subject, audio speakers for presenting audio stimuli, a combination of the aforementioned, or one or more other devices for producing or presenting sequences of stimuli to a subject. In some embodiments, sensors 206, are, optionally, mechanical, electrical, electromechanical, auditory (e.g., microphone), visual sensors (e.g., a digital video camera) or other type of sensors (e.g., a frontal brain electroencephalograph, and known as an EEG). The primary purpose of sensors 206 is to detect responses by a subject (e.g., subject 102 in FIG. 1) to sequences of stimuli presented by actuators 204. Some types of sensors produce large amounts of raw data, only a small portion of which can be considered to be indicative of the user response. In such systems, computer 210 contains appropriate filters and/or software procedures for analyzing the raw data so as to extract "sensor signals" indicative of the subject's response to the stimuli. In embodiments in which sensors 206 includes an electroencephalograph (EEG), the relevant sensor signal from the EEG may be a particular component of the signals produced by the EEG, such as the contingent negative variation (CNV) signal or the readiness potential signal.

Feedback devices 208 are, optionally, any device appropriate for providing feedback to the subject (e.g., subject 102 in FIG. 1). In some embodiments, feedback devices 208 provide real time performance information to the subject corresponding to measurement results, which enables the subject to try to improve his/her anticipatory timing performance. In some embodiments, the performance information provides positive feedback to the subject when the subject's responses (e.g., to sequences of stimuli) are within a normal range of values. In some embodiments, the one or more feedback devices 208 may activate the one or more actuators 204 in response to positive performance from the subject, such as by changing the color of the visual stimuli or changing the pitch or other characteristics of the audio stimuli.

Figure 3:
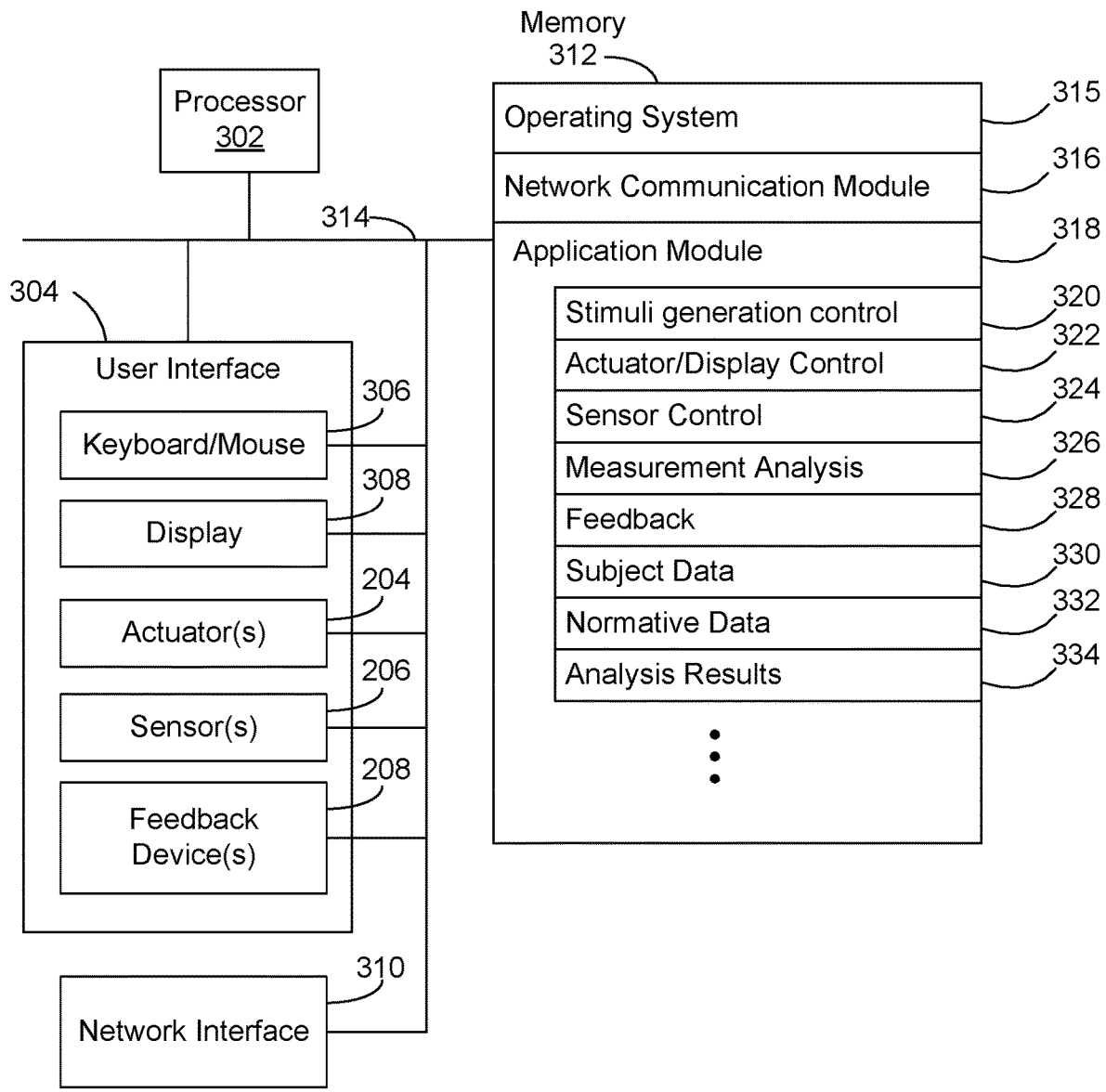
FIG. 3 is a detailed block diagram illustrating a cognition timing diagnosis and training system in accordance with some embodiments.

FIG. 3 is a block diagram of a cognition timing diagnosis and training (or remediation) system in accordance with some embodiments. The system includes one or more processors 302 (e.g., CPUs), user interface 304, memory 312, and one or more communication buses 314 for interconnecting these components. In some embodiments, the system includes one or more network or other communications interfaces 310, such as a network interface for conveying testing or training results to another system or device. The user interface 304 includes at least one or more actuators 204 and one or more sensors 206, and, in some embodiments, also includes one or more feedback devices 208. In some embodiments, the user interface 304 further includes additional computer interface devices such as keyboard/mouse 306 and display 308. In some embodiments, the display is coupled with one of actuators 204.

In some implementations, memory 312 includes a non-transitory computer readable medium, such as high-speed random access memory and/or non-volatile memory (e.g., one or more magnetic disk storage devices, one or more flash memory devices, one or more optical storage devices, and/or other non-volatile solid-state memory devices). In some implementations, memory 312 includes mass storage that is remotely located from processing unit(s) 302. In some embodiments, memory 312 stores an operating system 315 (e.g., Microsoft Windows, Linux or Unix), an application module 318, and network communication module 316.

In some embodiments, application module 318 includes stimuli generation control module 320, actuator/display control module 322, sensor control module 324, measurement analysis module 326, and, optionally, feedback module 328. Stimuli generation control module 320 generates sequences of stimuli, as described elsewhere in this document. Actuator/display control module 322 produces or presents the sequences of stimuli to a subject. Sensor control module 324 receives sensor signals and, where appropriate, analyzes raw data in the sensor signals so as to extract sensor signals indicative of the subject's (e.g., subject 102 in FIG. 1) response to the stimuli. In some embodiments, sensor control module 324 includes instructions for controlling operation of sensors 206. Measurement analysis module 326 analyzes the sensor signals to produce measurements and analyses, as discussed elsewhere in this document. Feedback module 328, if included, generates feedback signals for presentation to the subject via the one or more actuators or feedback devices.

In some embodiments, application module 318 furthermore stores subject data 330, which includes the measurement data for a subject, and analysis results 334 and the like. In some embodiments, application module 318 stores normative data 332, which includes measurement data from one or more control groups of subjects, and optionally includes analysis results 334, and the like, based on the measurement data from the one or more control groups.

Still referring to FIG. 3, in some embodiments, sensors 206 include one or more digital video cameras focused on the subject's pupil (e.g., digital video cameras 104), operating at a picture update rate of at least 200 hertz. In some embodiments, the one or more digital video cameras are infrared cameras, while in other embodiments, the cameras operate in other portions of the electromagnetic spectrum. In some embodiments, the resulting video signal is analyzed by processor 302, under the control of measurement analysis module 326, to determine the screen position(s) where the subject focused, and the timing of when the subject focused at one or more predefined screen positions.

In some embodiments, not shown, the system shown in FIG. 3 is divided into two systems, one which tests a subject and collects data, and another which receives the collected data, analyzes the data and generates one or more corresponding reports.

Figure 4A:
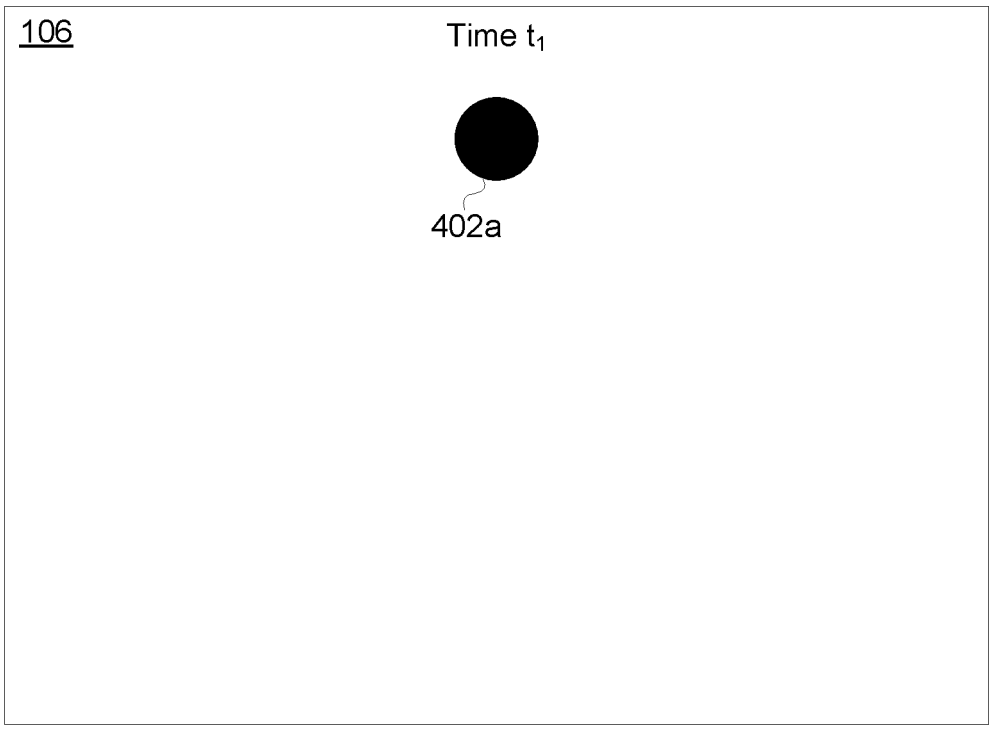
FIGS. 4A-4F illustrate a smoothly moving object, moving over a tracking path in accordance with some embodiments.
Figure 4B:
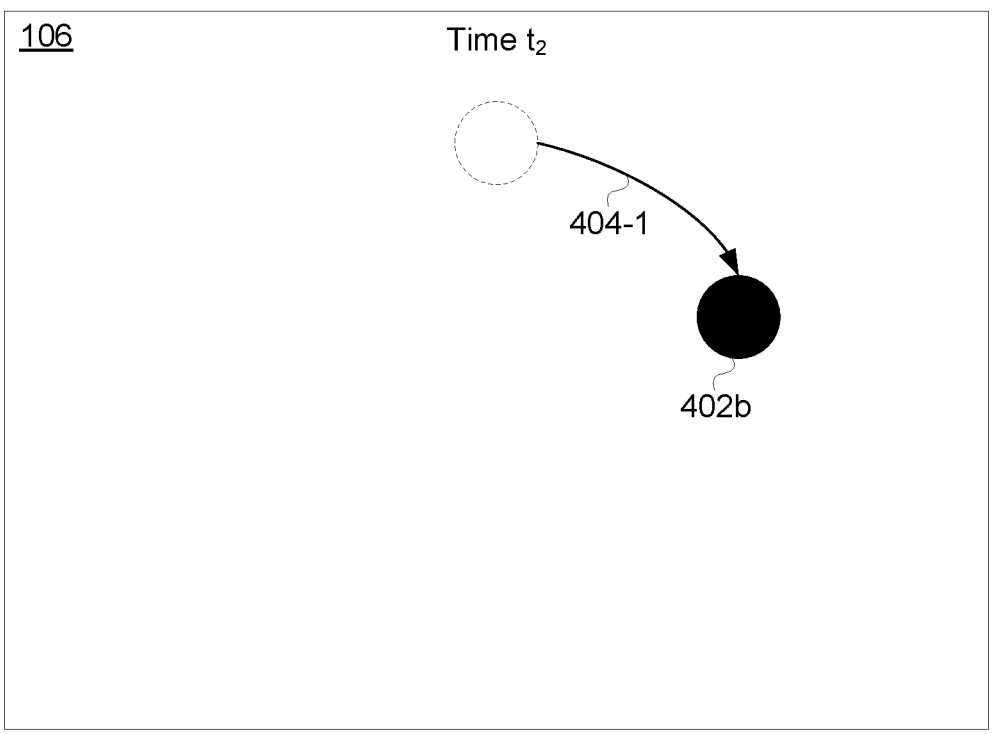
Figure 4C:
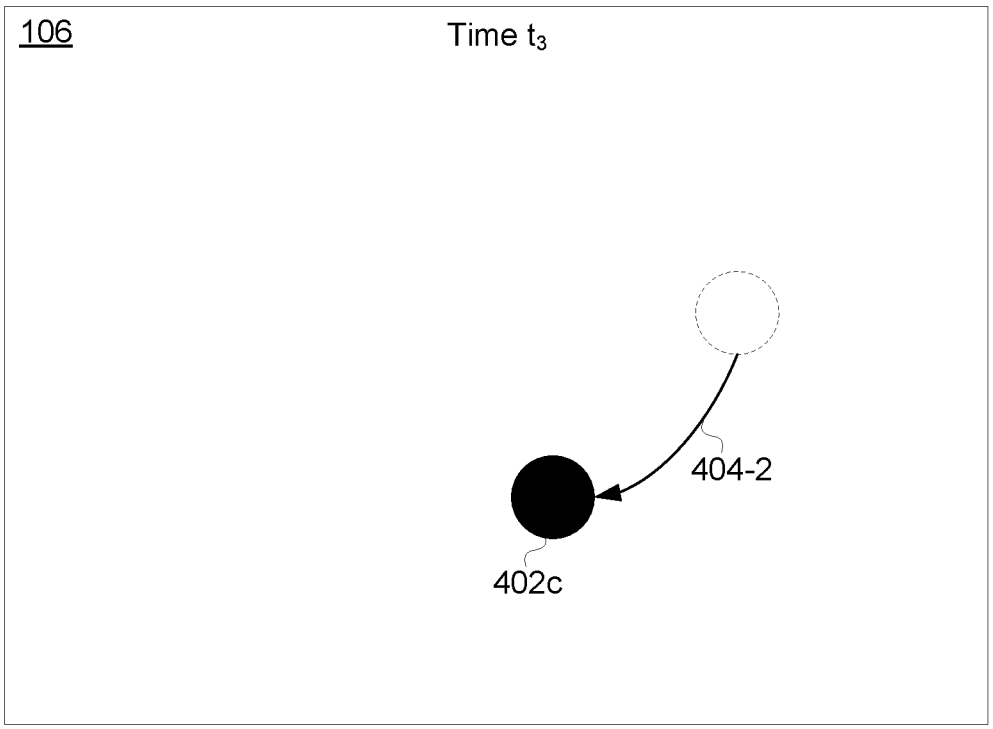
Figure 4D:
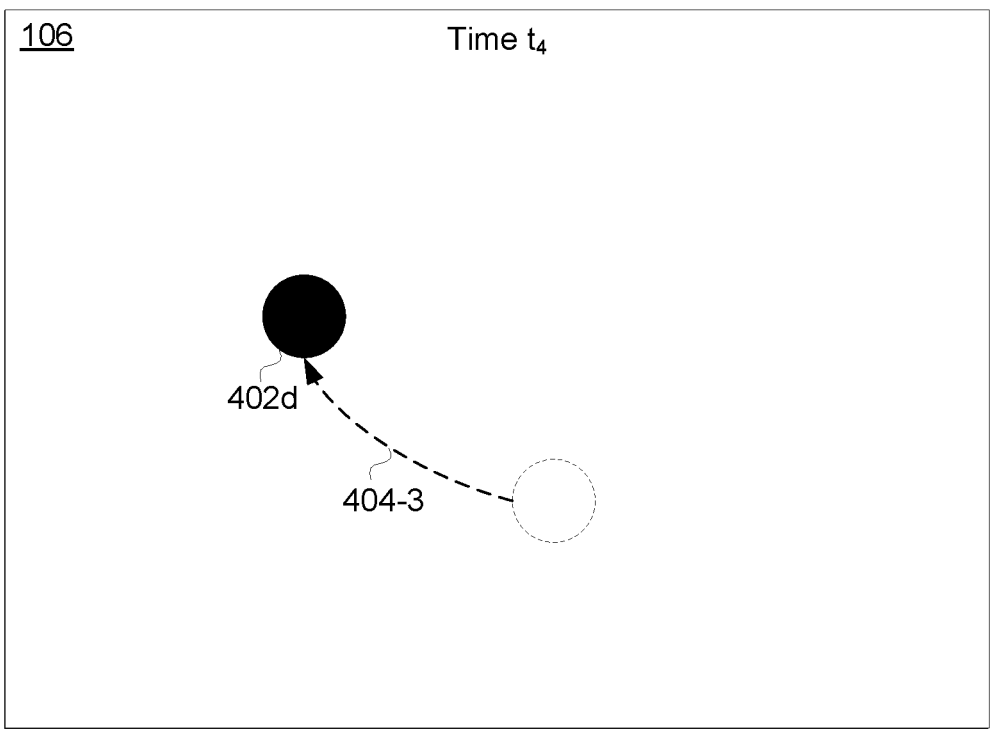
Figure 4E:
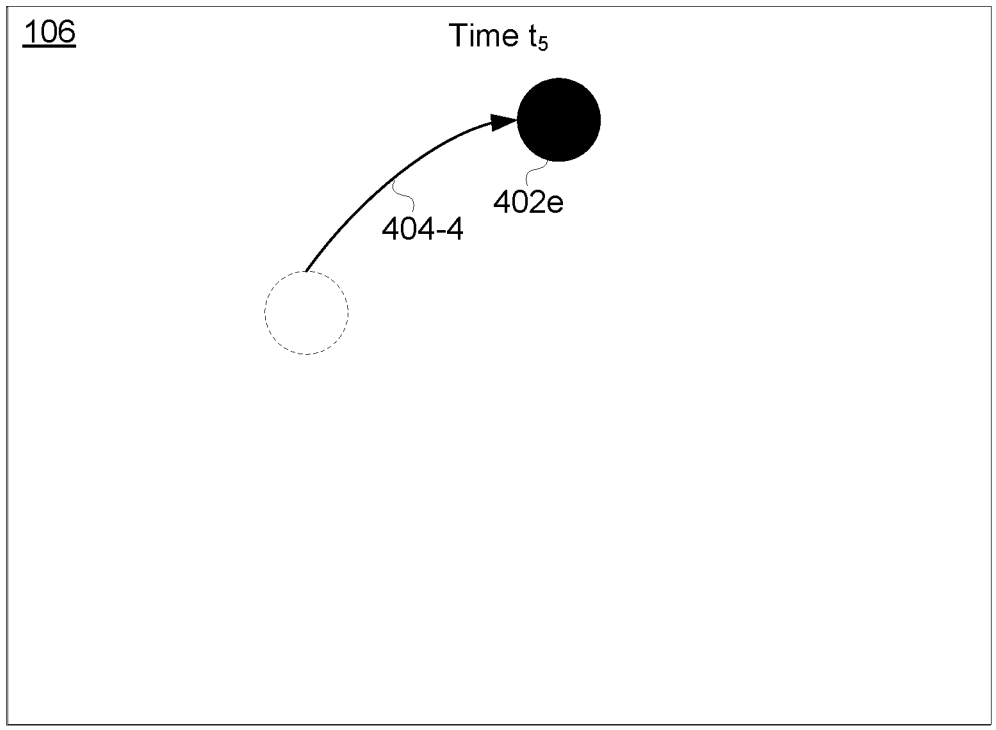
Figure 4F:
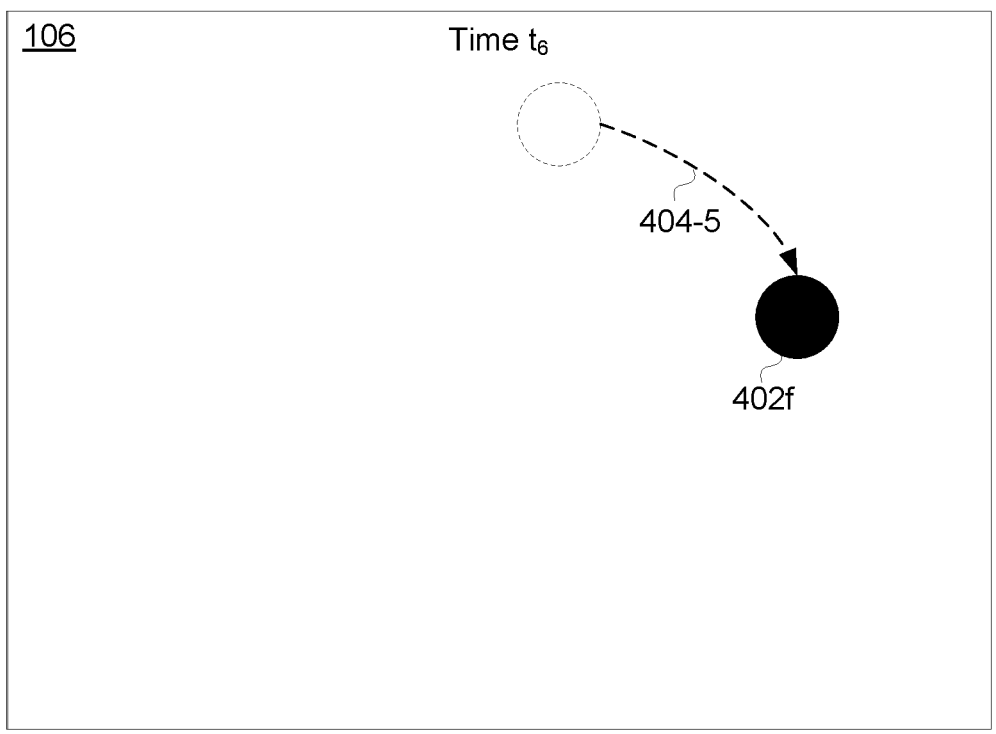

FIGS. 4A-4F illustrate a smoothly moving object, moving over a tracking path in accordance with some embodiments. FIG. 4A shows object 402 (e.g., a dot) at position 402a on display 106 at time $t_1$. FIG. 4B shows object 402 move along tracking path segment 404-1 to position 402b at time $t_2$. FIG. 4C shows object 402 move along tracking path segment 404-2 to position 402c at time $t_3$. FIG. 4D shows object 402 move along tracking path segment 404-3 to position 402d at time $t_4$. Tracking path segment 404-3 is shown as a dotted line to indicate that object 402 is not displayed while moving from position 402c to position 402d (e.g., tracking path segment 404-3 represents a gap in tracking path 404 of object 402). FIG. 4E shows object 402 move along tracking path segment 404-4 to position 402e at time $t_5$. In some embodiments, position 402e is position 402a and time $t_5$ represents the time it takes object 402 to complete one revolution (or orbit) along the tracking path. FIG. 4F shows object 402 move along tracking path segment 404-5 to position 402f at time $t_6$. In some embodiments, position 402f is position 402b. FIG. 4F further shows tracking path segment 404-5 as a dotted line to indicate that object 402 is not displayed while moving along it.

Figure 5A:
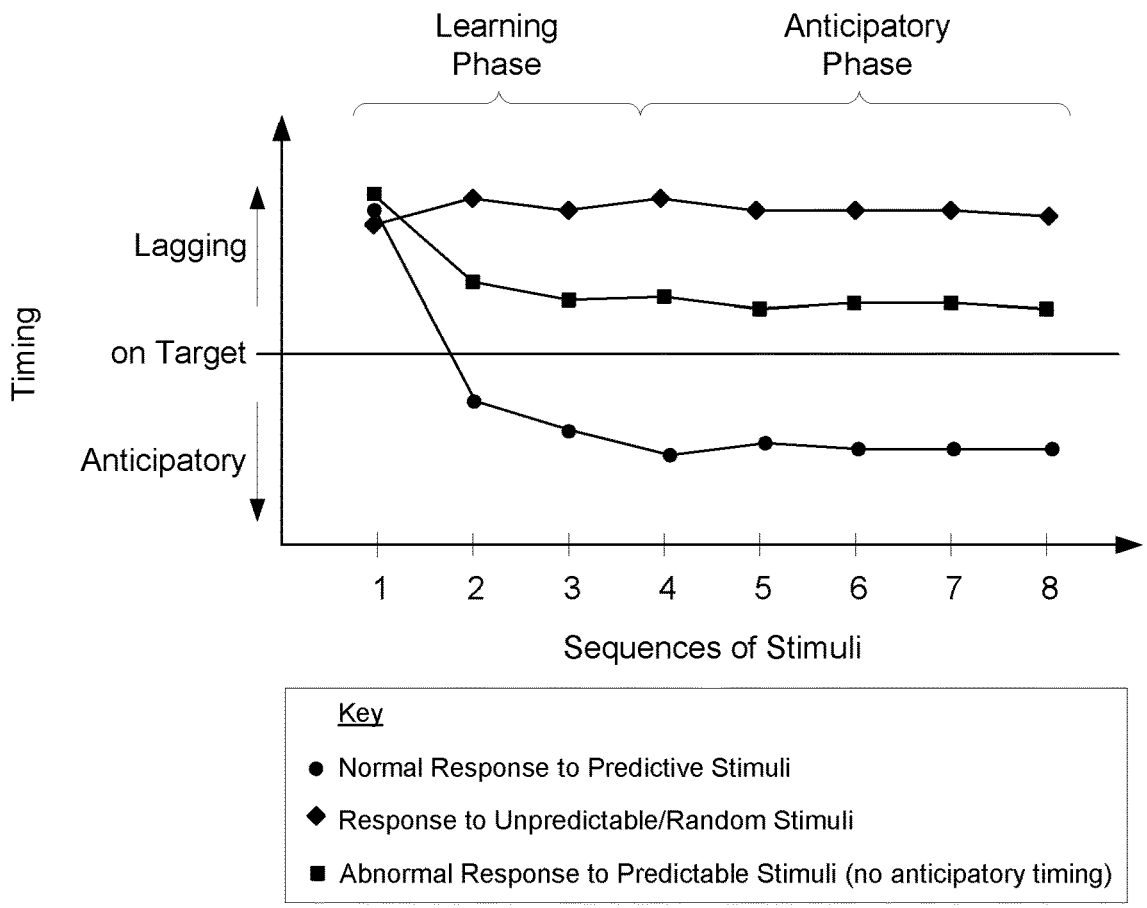
FIGS. 5A-5B shows normal and abnormal distributions of anticipatory timing in accordance with some embodiments.

FIG. 5A is a prophetic example of a graph of typical response timings to sequences of stimuli, both for predictable and random stimuli. For purposes of this discussion the terms "normal subject" and "abnormal subject" are defined as follows. Normal subjects are typically healthy individuals whose sensory-motor or anticipatory timing falls within a normal performance range. Abnormal subjects are individuals suffering from impaired brain function with respect to sensory-motor or anticipatory timing.

As represented in FIG. 5A, even normal, healthy subjects (hereinafter called "normal subjects" or "normal users") responding to random stimuli (♦) cannot anticipate the exact timing of the stimuli, and thus they lag behind being "on target." In other words, even after a learning phase where the user is subjected to a number of sequences of stimuli, the normal user cannot anticipate a subsequent sequence of random stimuli.

Normal subjects responding to predictable stimuli (●), such as a repeating sequence of visual stimuli, after a learning phase start to anticipate the stimuli before they are presented to the subjects. During a learning phase the normal subjects learn the sequence of stimuli and are then able to anticipate the stimuli during an anticipatory phase. Abnormal subjects (■), however, only slightly improve their response timing after the learning phase and still cannot anticipate the stimuli during the anticipatory phase. In other words, abnormal subjects may improve their response timing during training, but cannot anticipate subsequent stimuli as well as a typical normal subject.

Figure 5B:
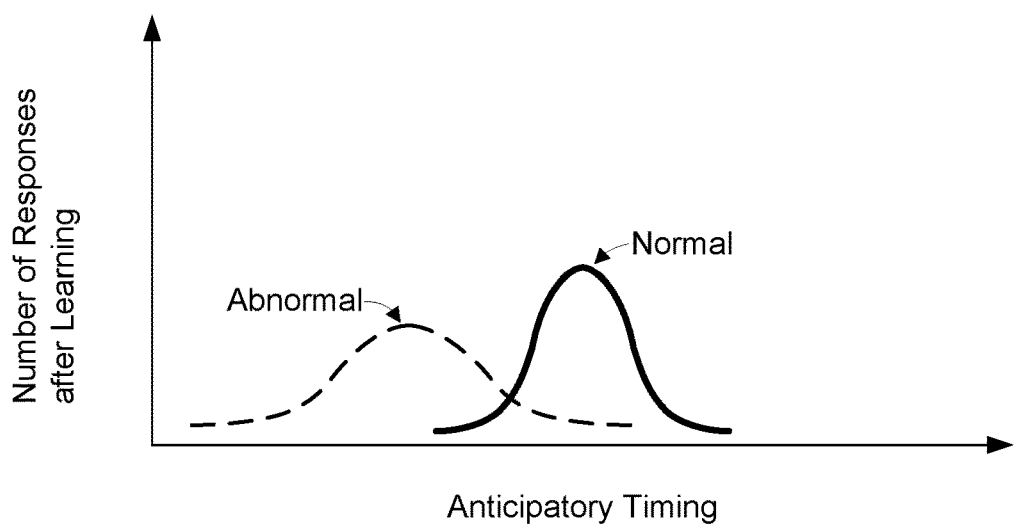

FIG. 5B is a prophetic example of the distribution of anticipatory response timing of an abnormal subject and the average anticipatory response timing of a control group of normal subjects. An abnormal distribution of anticipatory response timing is typically slower, on average than the normal distribution. The abnormal subject also typically has more inaccurate responses. Even more significantly, the width of an abnormal anticipatory timing distribution is typically significantly wider than the width of a normal anticipatory timing distribution. In some embodiments, the width of a distribution may be defined as the full width of the distribution at half maximum (sometimes called FWHM). In some embodiments, the width of a subject's anticipatory timing distribution is defined as the variance of the response distribution, the standard deviation of the response distribution, the average deviation of the response distribution, the coefficient of variation of the response distribution, or any other appropriate measurement of the width of the response distribution.

For example, in accordance with some embodiments, the subject's task is to follow an illuminated circle, which will alternate between two locations at a random (non-predictable) or non-random (predictable) rate. In some embodiments, the random rate is between 500 msec to 2 sec. The subject may indicate that the circle is illuminated at a particular location by activating a sensor, or by moving his/her eyes to focus on the illuminated circle on the screen. In another example, the subject may indicate that the circle is illuminated at a particular location by controlling the position of an image of an object on a screen using a joystick or other user input mechanism, and may be asked to move the object so as to "catch" a moving object, or to avoid being hit by another object, or to move the object so as to match the movement of a computer generated image, or other similar exercise.

In yet another example, multiple objects, such as images of circles, are displayed in a row or other pattern. The objects are flashed on and off in a predictable or random fashion. Eye movement reaction times are measured by a digital video infrared camera (e.g., digital video camera 104) focused on the subject's pupil, operating at a picture update rate of at least 200 hertz. The resulting digital video signal is analyzed by a computer to determine the screen position(s) where the subject was focusing, and the timing of when the subject focused at the appropriate screen position. If feedback is provided, the feedback may be provided by giving the subject a tone, using either open air audio speakers or headphones, or by having the color of the display change when the subject's anticipatory timing is within a normal or desired distribution.

In some embodiments, the stimuli presented to the subject include one or more sequences of non-predictable stimuli. The non-predictable stimuli can be random or pseudorandom sequences. The sequences of non-predictable stimuli cannot be learned and there is therefore no anticipatory timing by the subject. Measurements of the timing of the subject's responses to the sequences of non-predictable stimuli can be used as an internal control. These measurements are measurements of the subject's reactive timing. Subtracting the subject's reactive timing from the subject's anticipatory timing produces the subject's absolute anticipatory timing. By taking numerous timing measurements of the subject's responses to sequences of non-predictable stimuli, a distribution of such timing measurements is generated. The distribution can be graphed or displayed, compared with normative data for a population of other subjects, and the like.

Next, the stimuli presented to the subject also include multiple sequences of predictable stimuli. As discussed above, an initial phase in which the sequences of predictable stimuli are presented is called the learning phase. During the learning phase there is typically a progressive shift toward earlier correct reactions, and thus anticipatory timing. It is noted that in some embodiments, incorrect reactions by the subject are eliminated or not used for purposes of evaluating anticipatory timing. After the learning phase, there should be an anticipatory reaction phase during which the subject's response times are relatively static or fixed. The subject response times during the anticipatory reaction phase will generally be earlier than the initial responses during the learning phase. These response times, herein called anticipatory timing, will also be shorter than the subject's reactive timing to non-predictable stimuli.

By testing the subject with numerous sequences of predictable stimuli and taking measurements of the subject's anticipatory timing, a distribution of such timing is generated. The distribution can be graphed and compared with normative timing data for a population of other subjects as shown in FIG. 5B, and the like.

In some embodiments, the subject's reactive timing is subtracted from the subject's anticipatory timing to produce the subject's absolute anticipatory timing. In some embodiments, this is accomplished by subtracting an average reactive timing value from the anticipatory timing values.

The subject's absolute anticipatory timing distribution can be compared with the absolute anticipatory timing distribution of a control group of subjects. Both the average timing and the width of the timing distribution, as well as their comparison with the same parameters for a control group are indicative of whether the subject is suffering from a cognitive timing impairment.

In some embodiments, in order to provide accurate and meaningful real time measurements of where the user's is looking at any one point in time, the eye position measurements (e.g., produced via digital video cameras 104) are calibrated by having the subject focus on a number of points on a display (e.g., display 106) during a calibration phase or process. For instance, in some embodiments, calibration may be based on nine points displayed on the display, include a center point, positioned at the center of the display locations to be used during testing of the subject, and eight points along the periphery of the display region to be used during testing of the subject. In some embodiments, the eight points may correspond to locations having angular positions at 45 degree increments with respect to the center. The subject is asked to focus on each of the calibration points, in sequence, while digital video cameras (e.g., digital video cameras 104) measure the pupil and/or eye position of the subject. The resulting measurements are then used by a computer control system (e.g., computer control system 110) to produce a mapping of eye position to screen location, so that the system can determine the position of the display at which the user is looking at any point in time. In other embodiments, the number of points used for calibration may be more or less than nine points, and the positions of the calibration points may distributed on the display in various ways.

In some implementations, the calibration process is performed each time a subject is to be tested, because small differences in head position relative to the cameras, and small differences in position relative to the display 106, can have a large impact on the measurements of eye position, which in turn can have a large impact of the "measurement" or determination of the display position at which the subject is looking. The calibration process can also be used to verify that the subject (e.g., subject 102) has a sufficient range of oculomotor movement to perform the test.

Smooth Pursuit. In some embodiments, after calibration is completed, the subject is told to focus on an object (e.g., a dot or ball) on the display and to do his/her best to remain focused on the object as it moves. The displayed object is then smoothly moved over a path (e.g., a circular or oval path). In some embodiments, the rate of movement of the displayed object is constant for multiple orbits around the path. In various embodiments, the rate of movement of the displayed object, measured in terms of revolutions per second (i.e., Hertz), is as low as 0.1 Hz and as high as 10 Hz. However, it has been found that the most useful measurements are obtained when the rate of movement of the displayed object is in the range of about 0.4 Hz to 1.0 Hz, and more generally when the rate of movement of the displayed object is in the range of about 0.2 Hz to 2.0 Hz. A rate of 0.4 Hz corresponds to 2.5 seconds for the displayed object to traverse the tracking path, while a rate of 1.0 Hz corresponds to 1.0 seconds for the displayed object to traverse the tracking path. Even healthy subjects have been found to have trouble following a displayed object that traverses a tracking path at a repetition rate of more than about 2.0 Hz.

In some embodiments, the subject is asked to follow the moving object for eight to twenty clockwise circular orbits. For example, in some embodiments, the subject is asked to follow the moving object for twelve clockwise circular orbits having a rate of movement of 0.4 Hz, measured in terms of revolutions per second. Furthermore, in some embodiments, the subject is asked to follow the moving object for two or three sets of eight to twenty clockwise circular orbits, with a rest period between.

The angular amplitude of the moving object, as measured from the subject's eyes, is about 5 degrees in the horizontal and vertical directions. In other embodiments, the angular amplitude of the moving object is in the range of 3 to 10 degrees. The circular eye movement of the subject, while following the moving displayed object, can be divided into horizontal and vertical components for analysis. Thus, in some embodiments, four sets of measurements are made of the subject's eye positions while performing smooth pursuit of a moving object: left eye horizontal position, left eye vertical position, right eye horizontal position, and right eye vertical position. Ideally, if the subject perfectly tracked the moving object at all times, each of the four positions would vary sinusoidally over time. That is, a plot of each component (horizontal and vertical) of each eye's position over time would follow the function $\sin(\omega t+\theta)$, where $\sin(\ )$ is the sine function, $\theta$ is an initial angular position, and w is the angular velocity of the subject's eye. In some embodiments, one or two sets of two dimensional measurements (based on the movement of one or two eyes of the subject) are used for analysis of the subject's ability to visually track a smoothly moving displayed object. In some embodiments, the sets of measurements are used to generate a tracking metric by using smooth pursuit analysis. In some embodiments, the sets of measurements are used to generate a disconjugacy metric by using a binocular coordination analysis.

The optimal timeframe for each cycle or revolution of a smoothly moving target, for purposes of measuring a person's ability to visually follow a smoothly moving target, is related to the length of time that is experienced by the person as a single moment in time. A moment in time is experienced by most persons as a period having duration between 0.5 and 3 seconds. There is also evidence that if a subject concentrates on a difficult cognitive task, the present moment as experienced by the subject stretches out to a longer period of time, for example from 1 second to 2.5 seconds. The mechanism for this is the additional time needed to anticipate sensory information in more complex tasks.

In some embodiments, the video cameras (e.g., digital video cameras 104) take pictures of the subject's eye or eyes at least 400 times per second (i.e., the video cameras having a picture frame rate of at least 400 frames per second). For instance, in some embodiments, the video cameras take pictures of the subject's eye or eyes about 500 times per second, or about once every 2 milliseconds. Thus, during each orbit of the displayed object, the video cameras take between 200 and 1250 pictures of each eye, thereby providing a significant amount of data on which to base statistical analysis of the subject's ability to visually follow a smooth pursuit moving object. In some embodiments, the video cameras take thousands of pictures during each sets of revolutions of the displayed object, and thereby provide thousands of measurements of the subject's performance.

Smooth pursuit eye movement is an optimal movement to assess anticipatory timing in intentional attention (interaction) because it requires attention. Measurements of the subject's point of focus while attempting to smoothly pursue a moving displayed object can be analyzed for binocular coordination so as to generate a disconjugacy metric. Furthermore, as discussed in more detail in published U.S. Patent Publication 2006/0270945 A1, which is incorporated by reference in its entirety, measurements of a subject's point of focus while attempting to smoothly pursue a moving displayed object can also be analyzed so as to provide one or more additional metrics, such as a tracking metric, a metric of attention, a metric of accuracy, a metric of variability, and so on.

In accordance with some implementations, for each block of N revolutions or orbits of the displayed object, the pictures taken by the cameras are converted into display locations (hereinafter called subject eye positions), indicating where the subject was looking at each instant in time recorded by the cameras. In some embodiments, the subject eye positions are compared with the actual displayed object positions. In some embodiments, the data representing eye and object movements is low-pass filtered (e.g., at 50 Hz) to reduce signal noise. In some embodiments, saccades, which are fast eye movements during which the subject catches up with the moving displayed object, are detected and counted. In some embodiments, eye position measurements during saccades are replaced with extrapolated values, computed from eye positions preceding each saccade. In some other embodiments, eye position and velocity data for periods in which saccades are detected are removed from the analysis of the eye position and velocity data. The resulting data is then analyzed to generate one or more of the derived measurements or statistics discussed below.

Disconjugacy of Binocular Coordination. Many people have one dominate eye (e.g., the right eye) and one subservient eye (e.g., the left eye). For these people, the subservient eye follows the dominate eye as the dominate eye tracks an object (e.g., object 103 in FIG. 1, or object 402 in FIGS. 4A-4F). In some embodiments, a disconjugacy metric is calculated to measure how much the subservient eye lags behind the dominate eye while the dominate eye is tracking an object. Impairment due to sleep deprivation, aging, alcohol, drugs, hypoxia, infection, clinical neurological conditions (e.g., ADHD, schizophrenia, and autism), and/or brain trauma (e.g., head injury or concussion) can increase the lag (e.g., in position or time) or differential (e.g., in position or time) between dominate eye movements and subservient eye movements, and/or increase the variability of the lag or differential, and thereby increase the corresponding disconjugacy metric.

In some embodiments, the disconjugacy of binocular coordination is the difference between the left eye position and the right eye position at a given time, and is calculated as:

$$\text{Disconj}(t) = \text{POS}_{LE}(t) - \text{POS}_{RE}(t)$$

where "t" is the time and "$\text{POS}_{LE}(t)$" is the position of the subject's left eye at time t and "$\text{POS}_{RE}(t)$" is the position of the subject's right eye at time t. In various embodiments, the disconjugacy measurements include one or more of: the difference between the left eye position and the right eye position in the vertical direction (e.g., $\text{POS}_{RE_x}(t)$ and $\text{POS}_{LE_x}(t)$); the difference between the left eye position and the right eye position in the horizontal direction (e.g., $\text{POS}_{RE_y}(t)$ and $\text{POS}_{LE_y}(t)$); the difference between the left eye position and the right eye position in the two-dimensional horizontal-vertical plane (e.g., $\text{POS}_{RE_{xy}}(t)$ and $\text{POS}_{LE_{xy}}(t)$); and a combination of the aforementioned.

In some embodiments, a test includes three identical trials of 12 orbits. To quantify the dynamic change of disconjugacy during a test, the data from each trial is aligned in time within each test and the standard deviation of disconjugate eye positions (SDDisconj) is calculated. In accordance with some embodiments, SDDisconj for a set of "N" values is calculated as:

$$\text{SDDisconj}_N = \sqrt{\frac{1}{N}\sum_{i=1}^{N}(x_i - \langle x \rangle)^2}$$

where "x" is a disconjugate measurement discusssed above (e.g., Disconj(t)) and "⟨x⟩" represents the average value of the disconjugate eye positions. Thus, in various embodiments, $\text{SDDisconj}_N$ represents: the standard deviation of disconjugate eye positions in the vertical direction; the standard deviation of disconjugate eye positions in the horizontal direction; or the standard deviation of disconjugate eye positions in the two-dimensional horizontal-vertical plane. In some embodiments, a separate SDDisconj measurement is calculated for two or more of the vertical direction, the horizontal direction, and the two-dimensional horizontal-vertical plane.

Therefore, in various embodiments, disconjugacy measurements, standard deviation of disconjugacy measurements, tracking measurements, and related measurements (e.g., a variability of eye position error measurement, a variability of eye velocity gain measurement, an eye position error measurement, a rate or number of saccades measurement, and a visual feedback delay measurement) are calculated. Furthermore, in various embodiments, the disconjugacy measurements, standard deviation of disconjugacy measurements, tracking measurements, and related measurements are calculated for one or more of: the vertical direction; the horizontal direction; the two-dimensional horizontal-vertical plane; and a combination of the aforementioned.

In some embodiments, one or more of the above identified measurements are obtained for a subject and then compared with the derived measurements for other individuals. In some embodiments, one or more of the above identified measurements are obtained for a subject and then compared with the derived measurements for the same subject at an earlier time. For example, changes in one or more derived measurements for a particular person are used to evaluate improvements or deterioration in the person's ability to anticipate events. Distraction and fatigue are often responsible for deterioration in the person's ability to anticipate events and can be measured with smooth pursuit eye movements. In some embodiments, decreased attention, caused by fatigue or a distractor, can be measured by comparing changes in one or more derived measurements for a particular person. In some embodiments, decreased attention can be measured by monitoring error and variability during smooth eye pursuit.

Figure 6A:
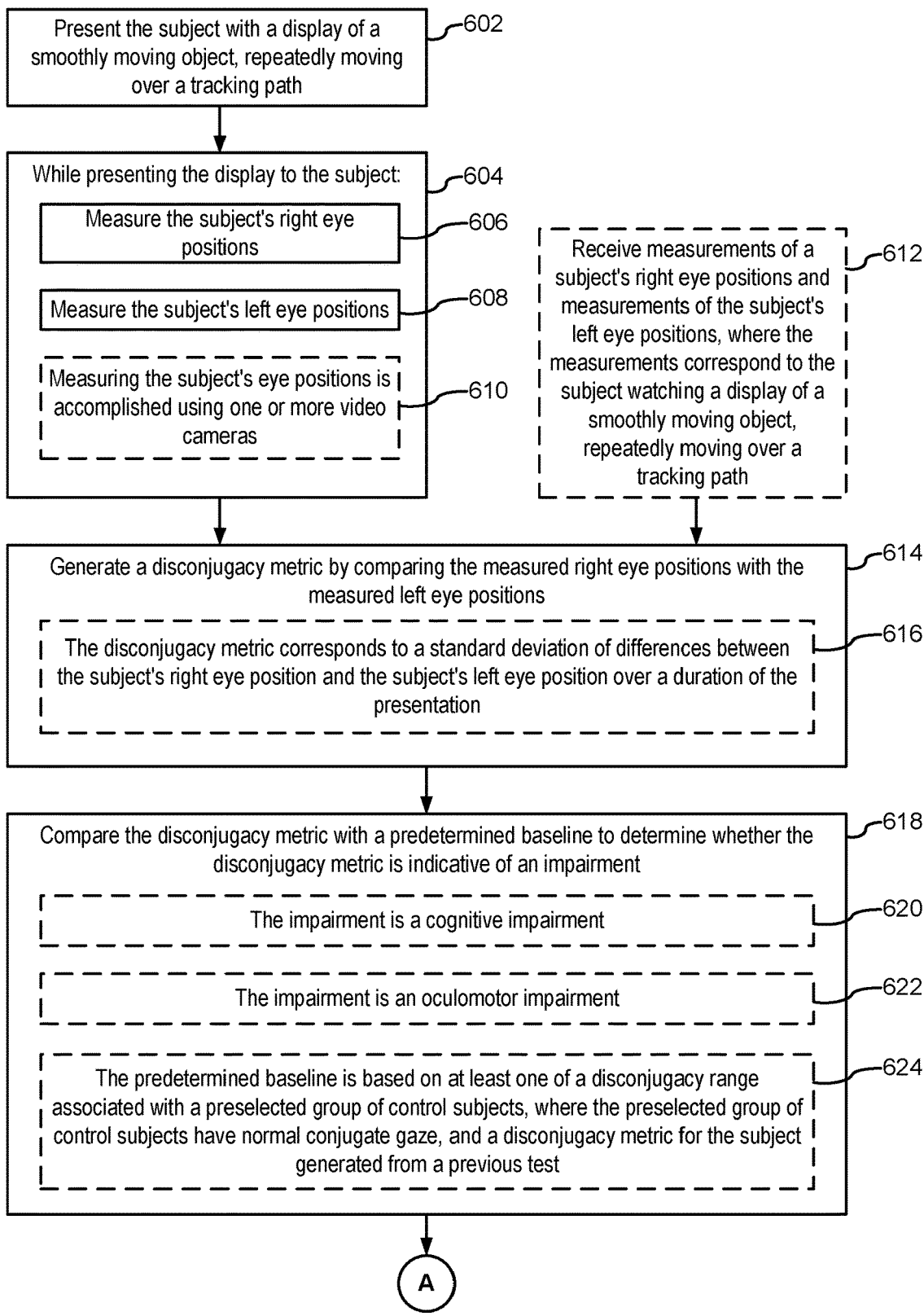
FIGS. 6A-6B are flow diagrams illustrating a method for impairment diagnosis using binocular coordination analysis in accordance with some embodiments.
Figure 6B:
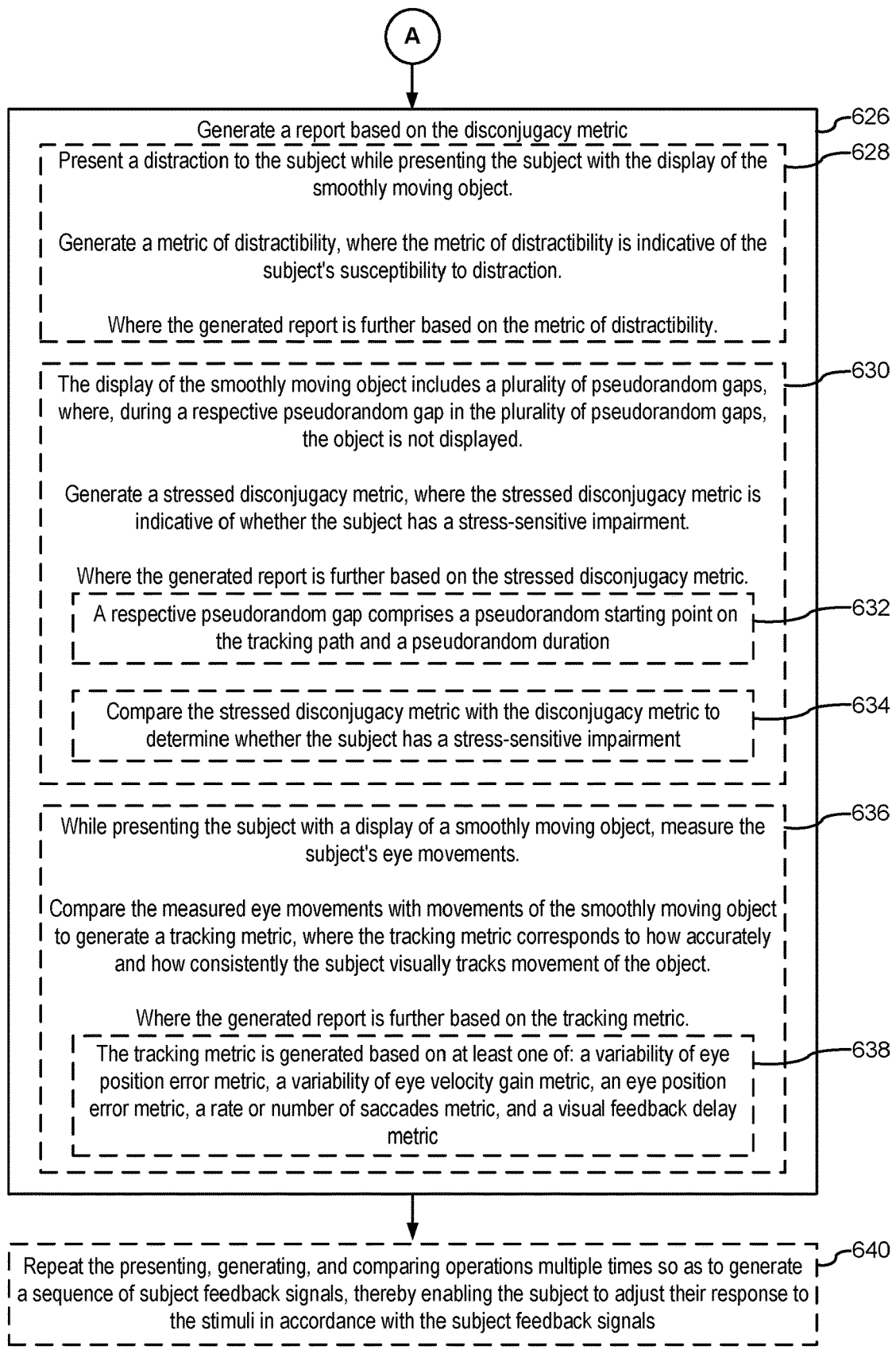

Diagnostic Method. FIGS. 6A-6B are flow diagrams representing a method for impairment diagnosis using binocular coordination analysis, in accordance with some embodiments. The methods are, optionally, governed by instructions that are stored in a computer memory or non-transitory computer readable storage medium (e.g., memory 312 in FIG. 3) and that are executed by one or more processors (e.g., processor 302) of one or more computer systems, including, but not limited to, the computer control system 110, and/or computer 210. The computer readable storage medium may include a magnetic or optical disk storage device, solid state storage devices such as Flash memory, or other non-volatile memory device or devices. The computer readable instructions stored on the computer readable storage medium may include one or more of: source code, assembly language code, object code, or other instruction format that is interpreted by one or more processors. In various implementations, some operations in each method may be combined and/or the order of some operations may be changed from the order shown in the figures. Also, in some implementations, operations shown in separate figures and/or discussed in association with separate methods may be combined to form other methods, and operations shown in the same figure and/or discussed in association with the same method may be separated into different methods. Moreover, in some implementations, one or more operations in the methods are performed by modules of cognitive diagnosis and training system 200 and/or the system shown in FIG. 3, including, for example, operating system processor 302, user interface 304, memory 312, network interface 310, and/or any sub modules thereof.

FIGS. 6A-6B illustrate method 600 for impairment diagnosis using binocular coordination analysis, in accordance with some embodiments. In some implementations, method 600 is performed at a system including one or more processors and memory storing instructions for execution by the one or more processors (e.g., system 200). The system presents (602) the subject with a display of a smoothly moving object, repeatedly moving over a tracking path. The rate of movement, the path over which the object moves, the periods of time over which the object is displayed, and the apparatus used to accomplish these functions are described above. For example, FIG. 1 shows subject 102 presented with display 106. Furthermore, display 106 includes object 103 moving along a circular path.

While presenting the display to the subject (604), the system measures (606) the subject's right eye positions and the system measures (608) the subject's left eye positions. For example, FIG. 1 shows subject 102 presented with display 106 including object 103. FIG. 1 further shows digital video cameras 104 for measuring subject 102's eye positions.

In some embodiments, measuring the subject's eye positions is accomplished (610) by using one or more video cameras. In accordance with these embodiments, FIG. 1 shows a system including digital video cameras 104 for measuring subject 102's eye positions.

In some embodiments, the system receives (612) measurements of the subject's right eye positions and measurements of the subject's left eye positions, where the measurements correspond to the subject watching a display of a smoothly moving object, repeatedly moving over a tracking path. In some embodiments, the system receives the measurements from a remote system or device. In some embodiments, the system receives the measurements from a user.

The system generates (614) a disconjugacy metric by comparing the measured right eye positions with the measured left eye positions. In some embodiments, generating the disconjugacy metric includes calculating a difference metric by subtracting the relative position of the subject's right eye from the relative position of the subject's left eye. In some embodiments, generating the disconjugacy metric includes averaging over each of a plurality of difference metrics, where each difference metric corresponds to a distinct time. In some embodiments, generating the disconjugacy metric includes generating a vertical metric and generating a horizontal metric, where generating a vertical metric includes measuring the difference between the subject's eyes along a vertical axis and generating a horizontal metric includes measuring the difference between the subject's eyes along a horizontal axis.

In some embodiments, the disconjugacy metric corresponds (616) to a standard deviation of differences between the subject's right eye position and the subject's left eye position over a duration of the presentation.

The system compares (618) the disconjugacy metric with a predetermined baseline to determine whether the disconjugacy metric is indicative of an impairment. In some embodiments, the impairment is (620) a cognitive impairment (e.g., an anticipatory timing impairment). For example, the impairment causes an inability to focus (e.g., ADHD). In some embodiments, the impairment is (622) an oculomotor impairment.

In some embodiments, the predetermined baseline is (624) based on at least one of: a disconjugacy range associated with a preselected group of control subjects, where the preselected group of control subjects have normal conjugate gaze, sometimes called a control group baseline; and a disconjugacy metric for the subject generated from a previous test, sometimes called an individual or personal baseline. In some embodiments, the group of control subjects is composed of persons having a similar age and socioeconomic status as the subject. In some embodiments, the group of control subjects is composed of persons having a similar brain development level as the subject. In some embodiments, the group of control subjects is composed of persons of the same gender as the subject. For example, in accordance with some implementations, the normal conjugate gaze range (e.g., the range representing 95% of population) is 0.2-0.7 without gaps and 0.25-1.0 with gaps (see discussion below regarding stressed disconjugacy metrics). In some accordance with implementations, an increase in the disconjugacy metric between subsequent tests may be indicative of fatigue, impaired mental state induced by drugs/alcohol, or recent trauma.

The system generates (626) a report based on the disconjugacy metric. In some embodiments, the system presents the report to the subject, test administrator or other user. In some embodiments, the report is stored in memory (e.g., stored in memory 312 as analysis results 334) for further analysis. In some embodiments, the report is used to generate a new baseline disconjugacy metric for future comparisons (e.g., the report is used to generate normative data 332 and/or subject data 330).

In some embodiments, the system presents (628) a distraction or stressor to the subject while presenting the subject with the display of the smoothly moving object. The system generates a metric of distractibility, where the metric of distractibility is indicative of the subject's susceptibility to distraction. The generated report is further based on the metric of distractibility. In some embodiments, the stressor is an unpredictable sound. For example, in some implementations, the sound is presented (e.g., through headphones or through speakers in the subject's room), unpredictably (e.g., at random or unpredictable times from the perspective of the subject), to the subject while the subject is presented with the display of the smoothly moving object. In some of these embodiments, the sound is loud enough to be distracting (e.g., 80 decibels) and each instance in which the sound is present lasts for a brief time (e.g., one second, or a period having a duration of 0.1 to 1.0 second). For example, in accordance with these embodiments, audio speakers 112 in FIG. 1 are used to present distracting noises during the presentation of object 103. In some embodiments, the stressor is a visual stimulus. For example, in some implementations, the visual stimulus is a bright flash on the display of the smoothly moving object at unpredictable times while the subject is presented with the display of the smoothly moving object.

In some embodiments, the display of the smoothly moving object includes (630) a plurality of pseudorandom gaps, where, during a respective pseudorandom gap in the plurality of pseudorandom gaps, the object is not displayed. The system generates a stressed disconjugacy metric, where the stressed disconjugacy metric is indicative of whether the subject has a stress-sensitive impairment (e.g., post-traumatic stress disorder (PTSD)). The generated report is further based on the stressed disconjugacy metric. In some embodiments, the display includes 10 gaps over a period of 30 seconds to a minute. In some embodiments, the pseudorandom gaps are random from the perspective of the subject. In some embodiments, the pseudorandom gaps are unknown in advance by the subject, but are on a preset schedule. FIGS. 4A-4F, for example, shows object 402 displayed on display 106 and moving along tracking path 404. Furthermore, FIG. 4D shows tracking path segment 404-3 as a dotted line to represent a first pseudorandom gap and FIG. 4F shows tracking path segment 404-5 as a dotted line to represent a second pseudorandom gap, in accordance with these embodiments.

In some embodiments, a respective pseudorandom gap comprises (632) a pseudorandom starting point on the tracking path and a pseudorandom duration. For example, in some embodiments, the pseudorandom starting point is selected from one of three potential starting points and the pseudorandom duration is selected from one of three potential durations (e.g., 100, 300, and 500 ms), where the selected starting point and selected duration are unknown in advance by the subject.

In some embodiments, the system compares (634) the stressed disconjugacy metric with the disconjugacy metric (for the same subject) to determine whether the subject has a stress-sensitive impairment (e.g., PTSD). For example, in accordance with some implementations, if the stressed disconjugacy metric is significantly higher than the disconjugacy metric (e.g., if the stressed disconjugacy metric exceeds the disconjugacy metric by more than a predefined threshold) then it indicates that the subject suffers from a stress-sensitive impairment (e.g., PTSD).

In some embodiments, while presenting the subject with a display of a smoothly moving object, the system measures (636) the subject's eye movements. The system compares the measured eye movements with movements of the smoothly moving object to generate a tracking metric, where the tracking metric corresponds to how accurately and how consistently the subject visually tracks movement of the object. The generated report is further based on the tracking metric. In some embodiments, the system measures both of the subject's eye movements. In some embodiments, the system measures the eye movements of one of the subject's eyes (e.g., the subject's dominate eye).

In some embodiments, the tracking metric is generated (638) based on at least one of: a variability of eye position error metric, a variability of eye velocity gain metric, an eye position error metric, a rate or number of saccades metric, and a visual feedback delay metric.

In some embodiments, the system repeats (640) the presenting, generating, and comparing operations multiple times so as to generate a sequence of subject feedback signals, thereby enabling the subject to adjust their response to the stimuli in accordance with the subject feedback signals. For example, the sequence of training steps 602-638 are repeatedly performed so as to help train a subject to improve his/her anticipatory timing. Such training exercises portions of the subject's brain that are responsible for cognitive tasks associated with anticipating events. By focusing the training narrowly on those cognitive tasks associated with anticipating events, appropriate portions of the brain are stimulated, which causes the brain to find ways to improve the subject's ability to anticipate the timing of predictable events. In some embodiments, only positive feedback signals are generated, to reward performance meeting predefined or individually determined performance goals. In other embodiments, the feedback signals include negative feedback signals that indicate failure to meet the performance goals. In still other embodiments the feedback signals may include gradations to indicate the extent to which the subject has met or failed to meet the performance goals. In some embodiments, smooth pursuit of a target moving over a circular path can be used for rehabilitative training as discussed in U.S. Patent Publication 2006/0270945 A1, which is incorporated by reference in its entirety.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

It will be understood that, although the terms "first," "second," etc. may be used herein to describe various elements, these elements should not be limited by these terms. These terms are only used to distinguish one element from another. For example, a first sound detector could be termed a second sound detector, and, similarly, a second sound detector could be termed a first sound detector, without changing the meaning of the description, so long as all occurrences of the "first sound detector" are renamed consistently and all occurrences of the "second sound detector" are renamed consistently. The first sound detector and the second sound detector are both sound detectors, but they are not the same sound detector.

The terminology used herein is for the purpose of describing particular implementations only and is not intended to be limiting of the claims. As used in the description of the implementations and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "upon a determination that" or "in response to determining" or "in accordance with a determination" or "upon detecting" or "in response to detecting" that the stated condition precedent is true, depending on the context.

What is claimed is:

1. A cognitive training system, comprising:
a measurement apparatus, comprising one or more cameras, to measure a subject's right eye positions and the subject's left eye positions;
a display; and
a computer control system coupled with the measurement apparatus and the display, the computer control system including one or more processors and memory, the memory storing one or more programs, the one or more programs comprising instructions to:
present to the subject, on the display, a smoothly moving object, repeatedly moving over a tracking path;
receive, while presenting to the subject the smoothly moving object on the display, from the measurement apparatus:
the subject's right eye positions; and
the subject's left eye positions;
generate a sequence of subject feedback signals, including repeatedly performing the operations of:
generating a disconjugacy metric for the subject based on a measure of variability of a plurality of differences between the measured right eye positions and corresponding measured left eye positions over a period of time while the object is moving;
comparing the disconjugacy metric with a predetermined baseline to determine whether the disconjugacy metric is indicative of an impairment; and
presenting the sequence of subject feedback signals to the subject, so as to train the subject to improve the subject's cognitive or anticipatory timing performance.

2. The cognitive training system of claim 1, wherein the sequence of subject feedback signals provides real-time performance information to the subject, including positive feedback provided to the subject when the subject's responses are within a normal range of values.

3. The cognitive training system of claim 2, wherein the smoothly moving object is presented, repeatedly moving over the tracking path, with a repetition rate of 0.2 to 2.0 Hz.

4. The cognitive training system of claim 1, wherein the smoothly moving object is presented, repeatedly moving over the tracking path, with a repetition rate of 0.2 to 2.0 Hz.

5. The cognitive training system of claim 4, wherein the disconjugacy metric corresponds to a standard deviation of the plurality of differences between the measured right eye positions and the corresponding measured left eye positions over the period of time.

6. The cognitive training system of claim 1, wherein the predetermined baseline is based on at least one of:
a disconjugacy range associated with a preselected group of control subjects, wherein the preselected group of control subjects have normal conjugate gaze; and
a disconjugacy metric for the subject generated from a previous test.

7. The cognitive training system of claim 1, the one or more programs including instructions to:
present a distraction to the subject while presenting to the subject the smoothly moving object; and
generate a metric of distractibility for the subject, wherein the metric of distractibility is distinct from the disconjugacy metric and is indicative of the subject's susceptibility to distraction.

8. The cognitive training system of claim 1, wherein the one or more programs further comprise instructions to:
present to the subject the smoothly moving object with a plurality of pseudorandom gaps, wherein, during a respective pseudorandom gap in the plurality of pseudorandom gaps, the object is not displayed; and
in accordance with the presentation of the smoothly moving object with the plurality of pseudorandom gaps, generate a stressed disconjugacy metric for the subject, wherein the stressed disconjugacy metric is distinct from the disconjugacy metric for the subject and is indicative of whether the subject has a stress-sensitive impairment.

9. The cognitive training system of claim 8, wherein a respective pseudorandom gap comprises a pseudorandom starting point on the tracking path and a pseudorandom duration.

10. The cognitive training system of claim 8, wherein the one or more programs include instructions to compare the stressed disconjugacy metric for the subject with the disconjugacy metric for the subject to determine whether the subject has a stress-sensitive impairment.

11. The cognitive training system of claim 1, the one or more programs including instructions to:
while presenting to the subject a display of a smoothly moving object, receive measurement of the subject's eye movements; and
compare the measured eye movements with movements of the smoothly moving object to generate a tracking metric for the subject, wherein the tracking metric corresponds to how accurately and how consistently the subject visually tracks movement of the object.

12. The cognitive training system of claim 1, wherein the measurement apparatus includes one or more video cameras.

* * * * *